United States Patent [19]

Haber et al.

[11] Patent Number: 5,433,191
[45] Date of Patent: Jul. 18, 1995

[54] MEDICATION SPRAYER

[75] Inventors: Terry M. Haber, Lake Forest; William H. Smedley, Lake Elsinore; Clark B. Foster, Laguna Niguel, all of Calif.

[73] Assignee: Habley Medical Technology Corp., Laguna Hills, Calif.

[21] Appl. No.: 163,603

[22] Filed: Dec. 6, 1993

Related U.S. Application Data

[63] Continuation of Ser. No. 883,878, May 15, 1992, abandoned.

[51] Int. Cl.⁶ .................. A61M 11/00; A61M 31/00
[52] U.S. Cl. ..................... 128/200.14; 128/200.22; 604/54
[58] Field of Search ............. 604/54, 24, 37, 38, 604/45; 128/200.14, 200.22–200.24, 203.12–203.15, 203.21, 203.23

[56] References Cited

U.S. PATENT DOCUMENTS

| | | | |
|---|---|---|---|
| 460,458 | 9/1891 | Bates | 128/200.14 |
| 904,149 | 11/1908 | Rachmann | 128/200.14 |
| 3,635,218 | 1/1972 | Ericson | 604/37 |
| 3,874,380 | 4/1975 | Baum | 128/200.14 |
| 3,874,381 | 4/1975 | Baum | 128/200.14 |
| 4,344,573 | 8/1982 | De Felice | 128/203.15 |
| 4,405,308 | 9/1983 | Jessup | 128/200.22 |
| 4,493,348 | 1/1985 | Lemmons | 604/54 |
| 4,743,243 | 5/1988 | Vaillancourt | 604/45 |
| 4,776,848 | 10/1988 | Solazzo | 604/54 |
| 4,923,448 | 5/1990 | Ennis, III | 128/200.22 |
| 5,331,954 | 7/1994 | Rex et al. | 128/207.18 |

Primary Examiner—Kimberly L. Asher
Attorney, Agent, or Firm—Townsend and Townsend Khourie and Crew

[57] ABSTRACT

A medication sprayer (2) is used to spray a liquid medication (110) directly from a vial (4) having a needle pierceable septum (6). The sprayer includes a body (10) reciprocally housing the vial. A spike assembly (60) includes an air inlet spike (66), connected to the ambient environment (108), and a liquid exit spike (68), both piercing the septum. The liquid exit spike is fluidly coupled to a piston/cylinder arrangement (88, 26, 36) having a combination piston/flapper valve (88) at one end of the cylinder (26) and a supplemental check valve (36) at the other end. The vial, spike assembly and piston/flapper valve move in unison to pump liquid through the piston/flapper valve into the cylinder, to pull air into the vial and to pump liquid in the cylinder through the supplemental check valve, past a spray nozzle (44) and into the ambient environment.

1 Claim, 4 Drawing Sheets

MEDICATION SPRAYER

This is a Continuation of application Ser. No. 07/883,878, filed May 15, 1992, now abandoned.

CROSS REFERENCE TO RELATED APPLICATIONS

This is related to U.S. patent application Ser. No. 07/747,299 filed Aug. 19, 1991 for Topical Sprayer With Remotely Actuated Spray Tip, and U.S. patent application Ser. No. 07/805,503 filed Dec. 9, 1991 for Syringe-Filling Medication Dispenser, both assigned to the assignee of the present invention, the disclosures of which are incorporated by reference.

BACKGROUND OF THE INVENTION

Many topical medications, including antiseptics, analgesics and anesthetics, are applied to reduce tactile sensation, cause numbing or aid in the healing process. Often, antifungal medications are also applied topically. Various types of hand held sprayers have been developed. However, many of them require specialized medication storage containers or require the transfer of the liquid medication from its storage container into the sprayer. The requirement of using specialized containers to store the liquid medication not only can increase cost but also may reduce the availability of certain medications in a topical spray form. The need to transfer a liquid medication from its initial, sterile container into the sprayer increases the possibility of contamination, exposes the liquid medication to oxygen, thus potentially reducing its shelf life, and also increases the risk of spilling the medication.

SUMMARY OF THE INVENTION

The present invention is directed to a medication sprayer which is simple in construction, easy to operate and permits liquid medication to be sprayed directly from a conventional vial of the type having a septum at one end.

The medication sprayer includes a hollow body which houses the vial for reciprocal axial movement within the body. Two hollow spikes, an air inlet spike and a liquid exit spike, are driven through the septum of the vial and into the interior of the vial. The air inlet spike is typically connected to the ambient environment while the liquid exit spike is fluidly coupled to a piston/cylinder arrangement.

The piston/cylinder arrangement preferably has a combination piston/flapper valve at one end of a piston and a supplemental check valve at the other end. Moving the combination piston/flapper valve within the cylinder away from the supplemental check valve during a return stroke, which, in the preferred embodiment, occurs by moving the vial axially along the interior of the body, causes a partial vacuum to be created within the cylinder. This pulls liquid from the vial into the cylinder while simultaneously causing air to enter into the vial, replacing the removed liquid, through the air inlet spike. The delivery stroke moves the combination piston/flapper valve towards the supplemental check valve to force the liquid medication in the cylinder through the supplemental check valve, past a spray nozzle and into the ambient environment.

Other features and advantages of the invention will appear from the following description in which the preferred embodiment has been set forth in detail in conjunction with the accompanying drawings.

DESCRIPTION OF THE PREFERRED EMBODIMENT

Figure 1:
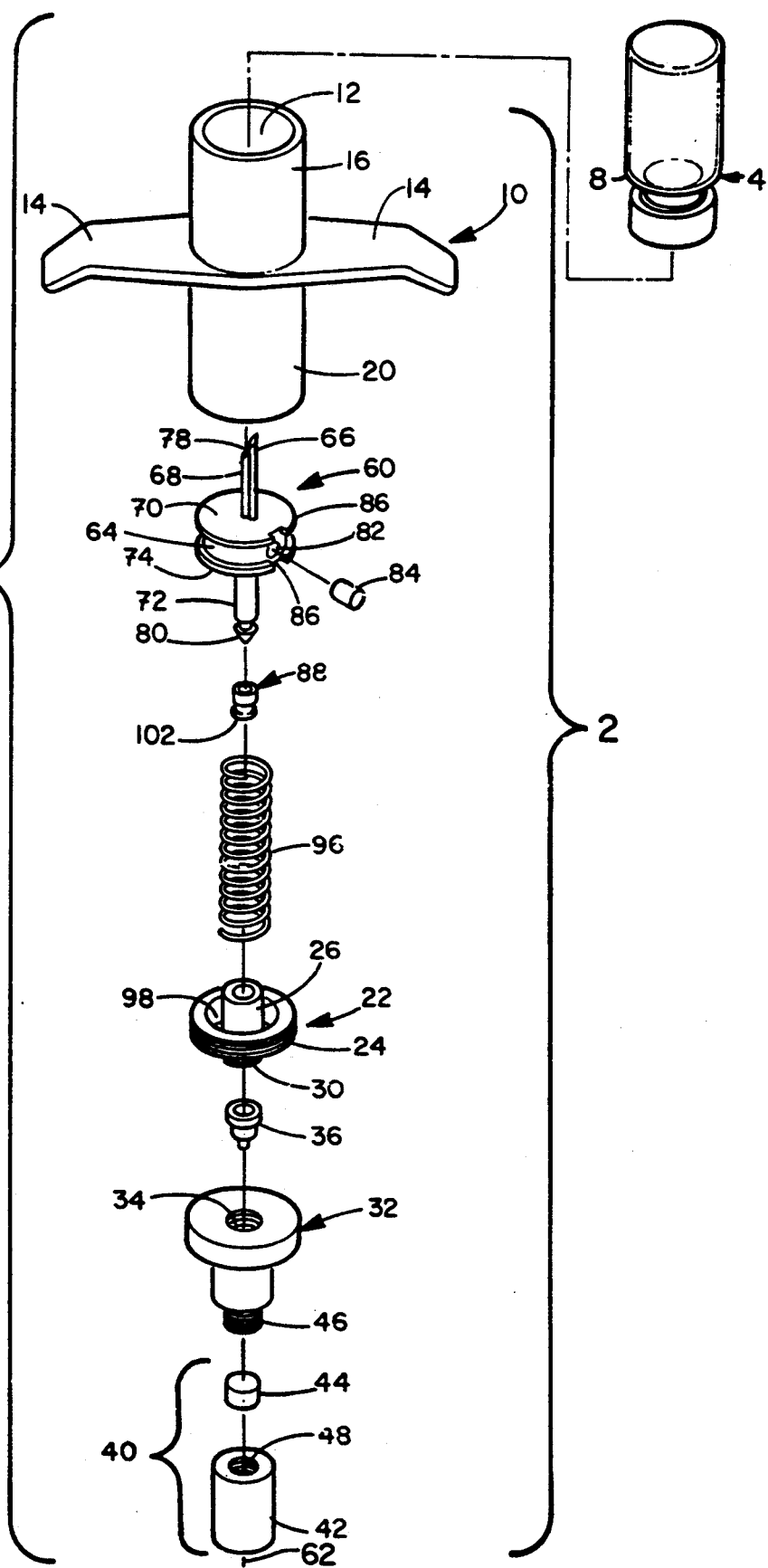
FIG. 1 is an exploded isometric view showing a medication sprayer made according to the invention in conjunction with a conventional vial.
Figure 2:
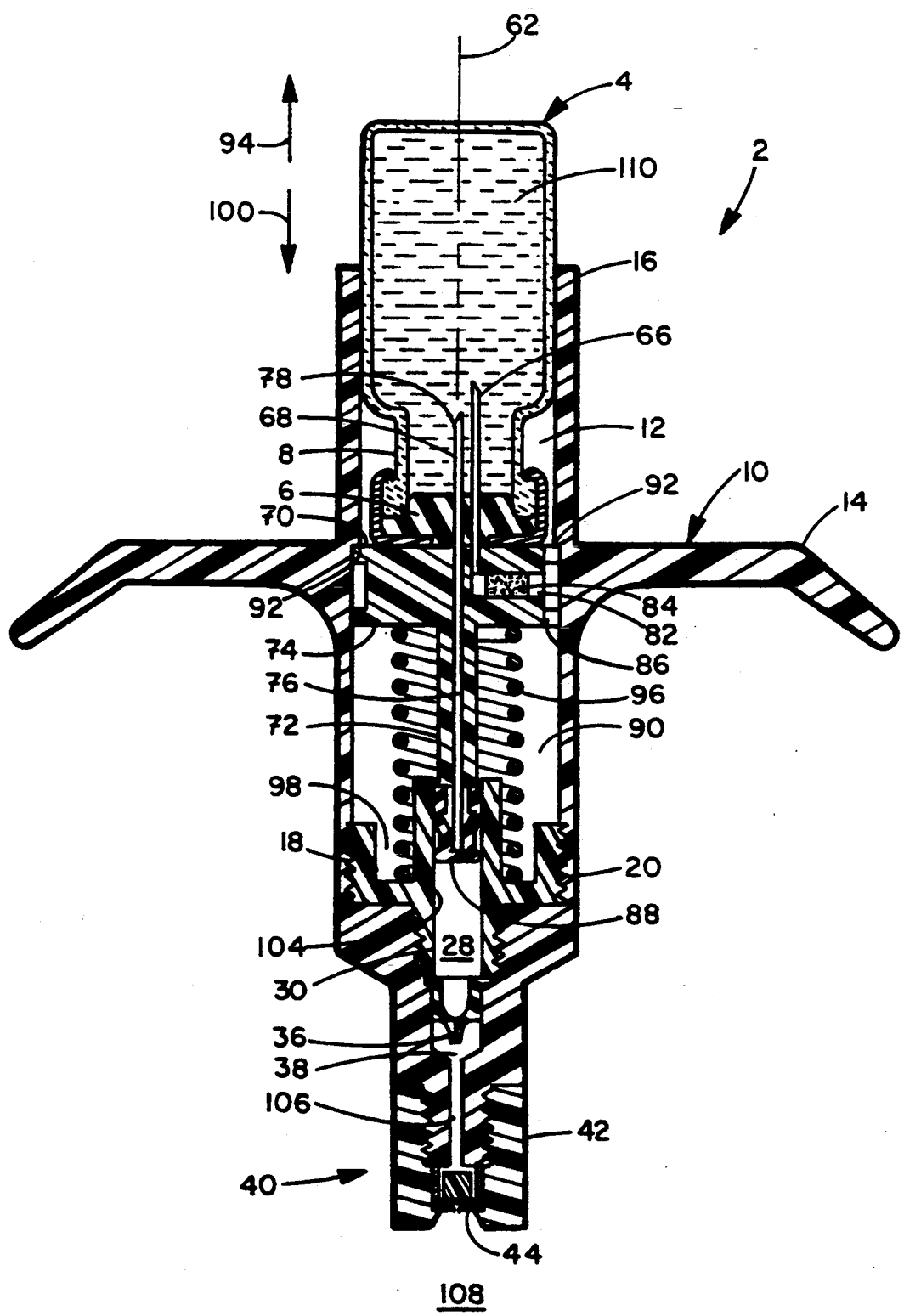
FIG. 2 shows the sprayer and vial of FIG. 1 in an assembled condition with the vial at the proximal position prior to a delivery stroke.

FIGS. 1 and 2 illustrate a medication sprayer 2 used with a conventional vial 4. Vial 4 is a type having a pierceable septum 6 at one end 8. Sprayer 2 includes a body 10 having a hollow interior 12 and a pair of outwardly extending finger ledges 14. Vial 4 and interior 12 are sized so that vial 4 sits within interior 12 and adjacent the proximal end 16 of body 10.

Figure 4:
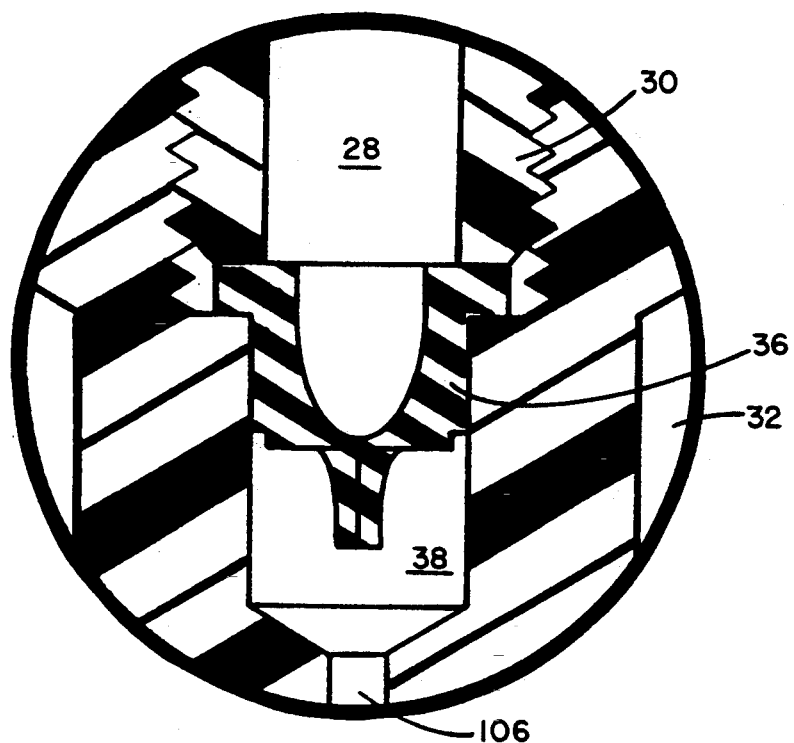
FIG. 4 is an enlarged view of a portion of the sprayer of FIG. 2 illustrating the duckbill-type supplemental check valve.
Figure 5:
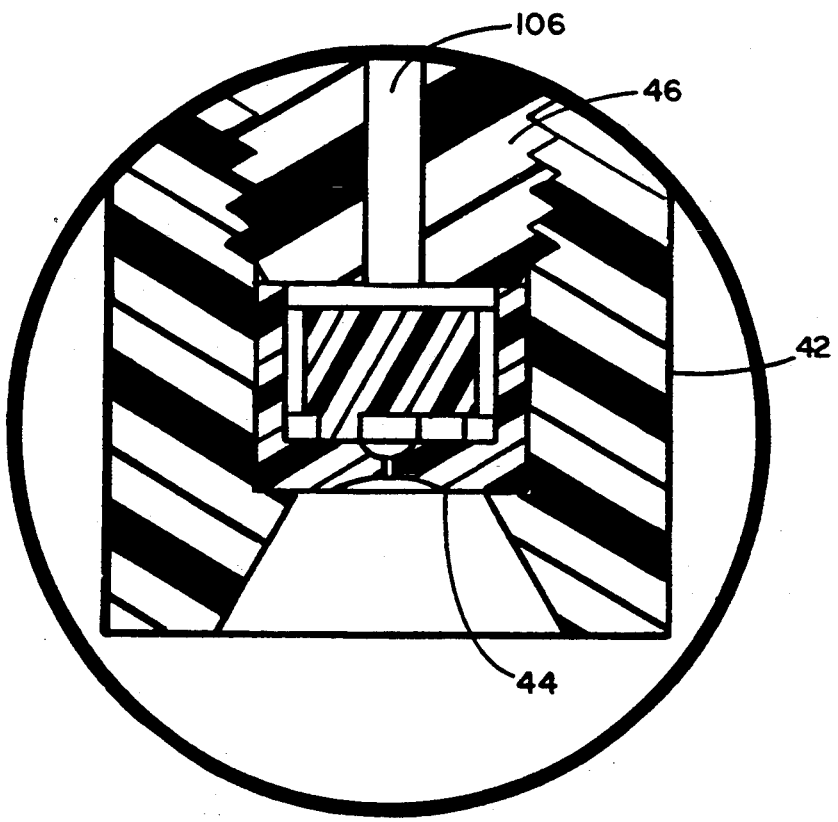
FIG. 5 is an enlarged view of a portion of the sprayer of FIG. 2 showing the nozzle.

Body 10 has internal threads 18 at the distal end 20 of the body. A pump cylinder assembly 22 has a threaded flange 24 sized to engage internal threads 18 of body 10. Pump cylinder assembly 22 includes a pump cylinder 26 which defines a variable volume pump cylinder bore 28 formed therein. Pump cylinder assembly 22 also includes a threaded tip 30 which extends past distal end 20. A check valve housing 32, having internal threads 34, is threadably mounted to threaded tip 30 to secure housing 32 to assembly 22 and body 10. Before doing so, a duckbill-type supplemental check valve 36, see FIG. 4, is secured between threaded tip 30 and check valve housing 32 within an open region 38 defined within housing 32.

A nozzle assembly 40, including a nozzle housing 42 and a nozzle 44, is mounted to a threaded tip 46 of housing 32 through the engagement of internal threads 48 formed in nozzle housing 42. Nozzle 44 is a conventional element such as nozzle insert no. 300029.001 made by Pfeiffer of Germany.

A pump assembly 60 is mounted within interior 12 of body 10 for movement parallel to an axis 62. Pump assembly 60 includes a disc-like spike support 64 to which an air inlet spike 66 and a liquid exit spike 68, both hollow, extend from the proximal end 70 of spike support 64. Pump assembly 60 also includes a shank 72 extending from the distal end 74 of spike support 64. Shank 72 is hollow so that a fluid pathway 76 is defined from the tip 78 of liquid exit spike 68 to the distal end 80 of shank 72. Air inlet spike 66 is also hollow and has its interior coupled to an air filter cavity 82 within which an air filter 84 is housed. Air filter 84 is used to filter the air which is drawn into vial 4 as discussed below. Filter 84 can be made of a variety of material such as cotton or foam. Free flow of air into cavity 82 is ensured by the provision of cutouts 86 adjacent cavity 82. A piston 88 is mounted to distal end 80 of shank 72 and is positioned for reciprocal movement within variable volume pump cylinder bore 28.

Interior 12 of body 10 includes an enlarged region 90 within which piston assembly 60 can move parallel to axis 62. Enlarged region 90 is bounded at one end by a radially inwardly extending ledge 92 against which proximal end 70 of pump assembly 60 presses when biased in the proximal direction 94 by a coil compression spring 96. Spring 96 is captured within an annular recess 98 created between pump cylinder 26 and threaded flange 24 so to normally bias spike assembly 60 against ledge 92.

Figure 3:
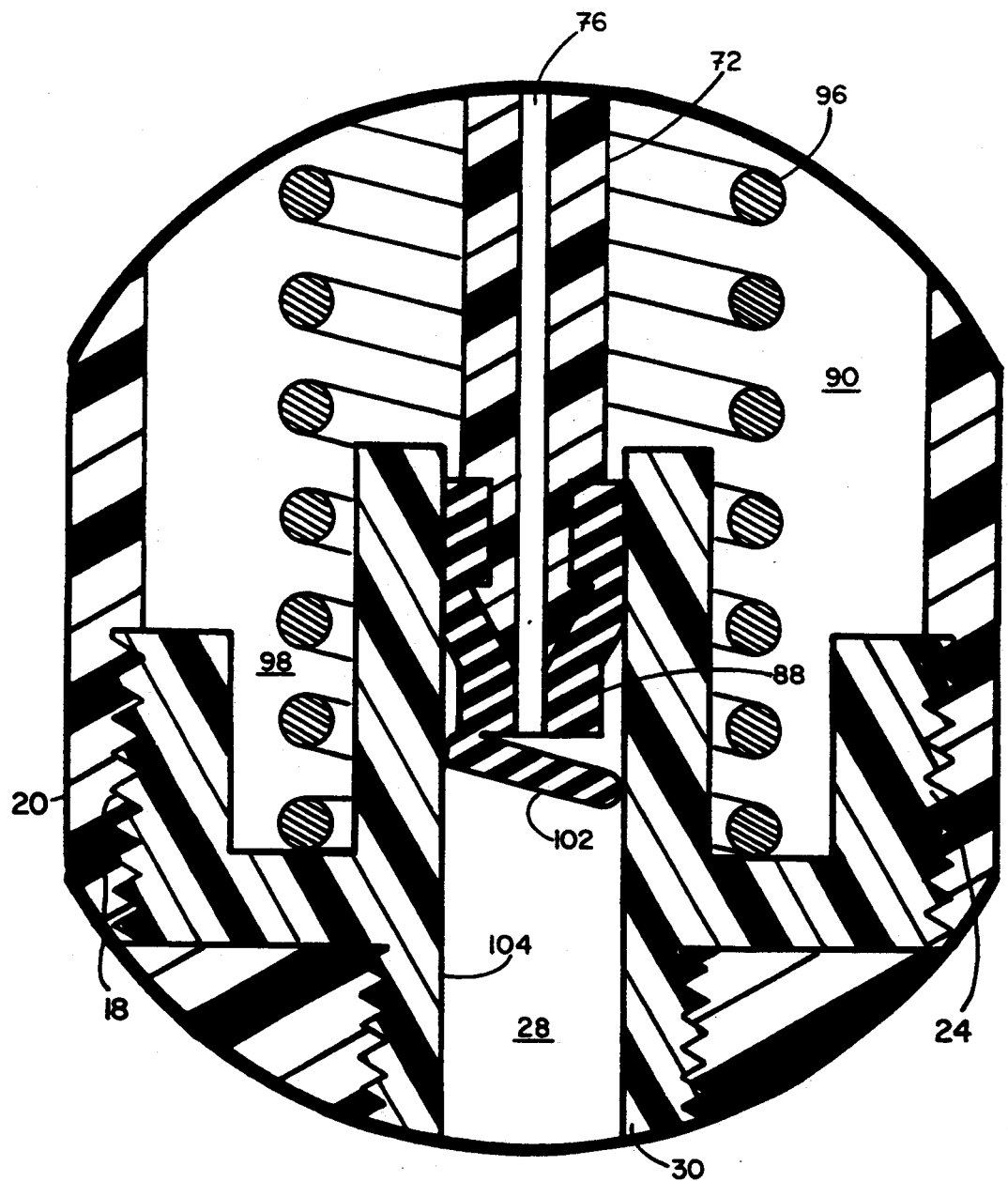
FIG. 3 is an enlarged view of a portion of the sprayer of FIG. 2 showing the flapper valve element in an open position.

To use medication sprayer 2, one inserts vial 4 through proximal end 16 of body 10 so that spikes 66, 68 pierce septum 6. Pressing vial 4 in the distal direction 100 causes vial 4 and piston assembly 60 to move in distal direction 100 to compress spring 96. This also causes piston 88 to move along pump cylinder 26 towards supplemental check valve 36 and decreases the volume of the variable volume bore 28. Movement in this direction causes a flapper valve element 102 attached to a distal end at the piston 88 to drag against the cylinder wall 104, thus sealing the distal end of fluid pathway 76. This creates a higher pressure region within variable volume cylinder bore 28 forcing any fluid within the variable volume cylinder bore through check valve 36, along a conduit 106 formed in check valve housing 32, past nozzle 44 and into an ambient environment 108. At the end of this delivery stroke, return spring 96 forces piston 88, piston assembly 60, and vial 4 in proximal direction 94 from a distal position to the proximal position of FIG. 2 during a return stroke. Doing so creates a partial vacuum within variable volume cylinder bore 28 which causes liquid medication 110 within vial 4 to pass through liquid exit spike 68, along fluid pathway 76, past piston 88 and into bore 28. Simultaneously, air is drawn into vial 4 through filter 84 and air inlet spike 66 to replace the liquid medication 110 drawn into variable volume bore 28. As shown in FIG. 3, the flapper element 102 frictionally engages the cylinder wall 102 with a friction thereby fluidly coupling the fluid path 76 and the variable volume bore 28. In this way, the pressure within vial 4 remains substantially at atmospheric pressure. If desired, air inlet spike 66 could be connected to a source of inert gas, such as nitrogen, in the event that liquid medication 110 is sensitive to oxygen degradation. Repeating the reciprocal movement of vial 4 causes liquid medication 110 to be sprayed from medication sprayer 2 into ambient environment 108. The friction between the cylinder wall and the flapper element 102 is sufficient and the flapper element 102 is constructed to cause the flapper element 102 to seal the cylinder 28 from the container when the piston 88 moves towards the distal position and to fluidly couple the cylinder 28 to the container when the piston 88 moves towards the proximal position.

Vial 4 is preferably a conventional glass vial. Most of the parts of sprayer 2 can be made of a medical grade plastic, such as polycarbonate. Spikes 66, 68 are medical grade stainless steel needles while return spring 96 is medical grade stainless steel as well. Piston 88 and supplemental check valve 36 are both silistac rubber. Other materials may be used as well.

Modification and variation can be made to the disclosed embodiment without departing from the subject of the invention as defined in the following claims.

What is claimed is:

1. A medication sprayer, for use with a container containing a liquid medication, the sprayer comprising:
   a body adapted to receive a container;
   dual port means for providing gas and liquid ports into the interior of a container;
   a nozzle carried by the body;
   delivery means for (a) pumping liquid medication from a container through the liquid port, (b) replacing the pumped liquid medication with a gas which passes into the container through the gas port, and (c) forcing liquid medication pumped from a container through the nozzle and into the ambient environment, the delivery means including a piston and cylinder assembly being adapted for actuation by reciprocal movement of thee container when a container mounted to the body, the piston and cylinder assembly including a cylinder and a piston adapted to be coupled to a container, for reciprocal movement with the container between a distal position and a proximal position, the cylinder having a cylinder wall, the delivery means also including a check valve fluidly coupling a container and the cylinder, the check valve including a flapper element which frictionally engages the cylinder wall as the piston moves between the distal position and the proximal position;
   the friction between the cylinder wall and the flapper element being sufficient and the flapper element constructed to cause the flapper element to seal the cylinder from a container when the piston moves towards the distal position and to fluidly couple the cylinder to a container when the piston moves towards the proximal position.

* * * * *